United States Patent
Lüth

[11] Patent Number: 5,188,529
[45] Date of Patent: Feb. 23, 1993

[54] DEVICE FOR STATIC FIXATION OF THE JAW RELATION

[75] Inventor: Stefan Lüth, Munich, Fed. Rep. of Germany

[73] Assignee: Girrbach Dental GmbH, Pforzheim, Fed. Rep. of Germany

[21] Appl. No.: 698,272

[22] Filed: May 10, 1991

[30] Foreign Application Priority Data

May 10, 1990 [DE] Fed. Rep. of Germany ....... 4014975

[51] Int. Cl.⁵ .............................................. A61C 19/04
[52] U.S. Cl. ......................................... 433/68; 433/69
[58] Field of Search ..................................... 433/68, 69

[56] References Cited

U.S. PATENT DOCUMENTS

| | | | |
|---|---|---|---|
| 1,734,398 | 11/1929 | Phillips | 433/69 |
| 1,776,474 | 9/1930 | Messerman | 433/68 |
| 2,451,766 | 10/1948 | Maylan | 433/69 |
| 2,552,829 | 5/1951 | Wilkinson | 433/68 |
| 2,562,106 | 7/1951 | Leathers | 433/69 |
| 2,841,871 | 7/1958 | Miller | 433/68 |
| 3,059,335 | 10/1962 | Reynolds | 433/69 |
| 4,797,097 | 1/1989 | Cohn | 433/64 |

FOREIGN PATENT DOCUMENTS

| | | |
|---|---|---|
| 0162991 | 4/1985 | European Pat. Off. . |
| 2825470 | 6/1978 | Fed. Rep. of Germany . |
| 7836938 | 3/1979 | Fed. Rep. of Germany . |
| 661720 | 11/1951 | United Kingdom ................. 433/68 |

Primary Examiner—Cary E. O'Connor
Assistant Examiner—Nicholas D. Lucchesi
Attorney, Agent, or Firm—Spensley, Horn, Jubas & Lubitz

[57] ABSTRACT

For static fixation of the jaw relation in intraoral recording, a recording instrument set is used that includes a pin holder with a vertically adjustable stylus for placement in one jaw, and a writing or recording plate with an alignment clamp mounted on it for placement in the other jaw. The stylus, initially vertically locked on the pin holder, can be locked in stationary fashion in the ascertained jaw relation in the alignment clamp. By means of this locking, the jaw relation is keyed, and the use of hardenable material such as molding plaster previously used for this purpose can be dispensed with. This dental treatment process can thus be done in less time and with less material, and once the jaw relation has been keyed it is retained reliably until further processing in the dental laboratory. This locking can be attained particularly advantageously if a pan bearing that receives the lower end of the stylus, embodied as a writing ball, is provided in the alignment clamp. This affords simple options for locking that are based essentially on the fact that after the introduction of the writing ball the entry cross section of the pan bearing is reduced far enough that the writing ball is firmly retained in the pan bearing.

10 Claims, 2 Drawing Sheets

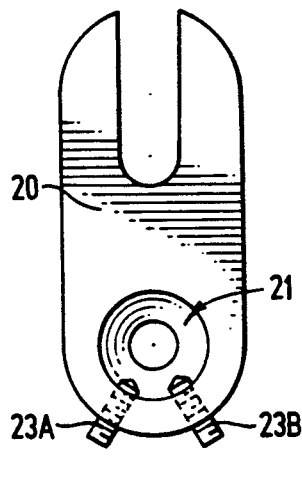
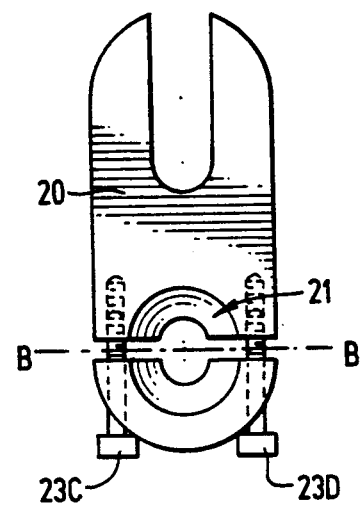
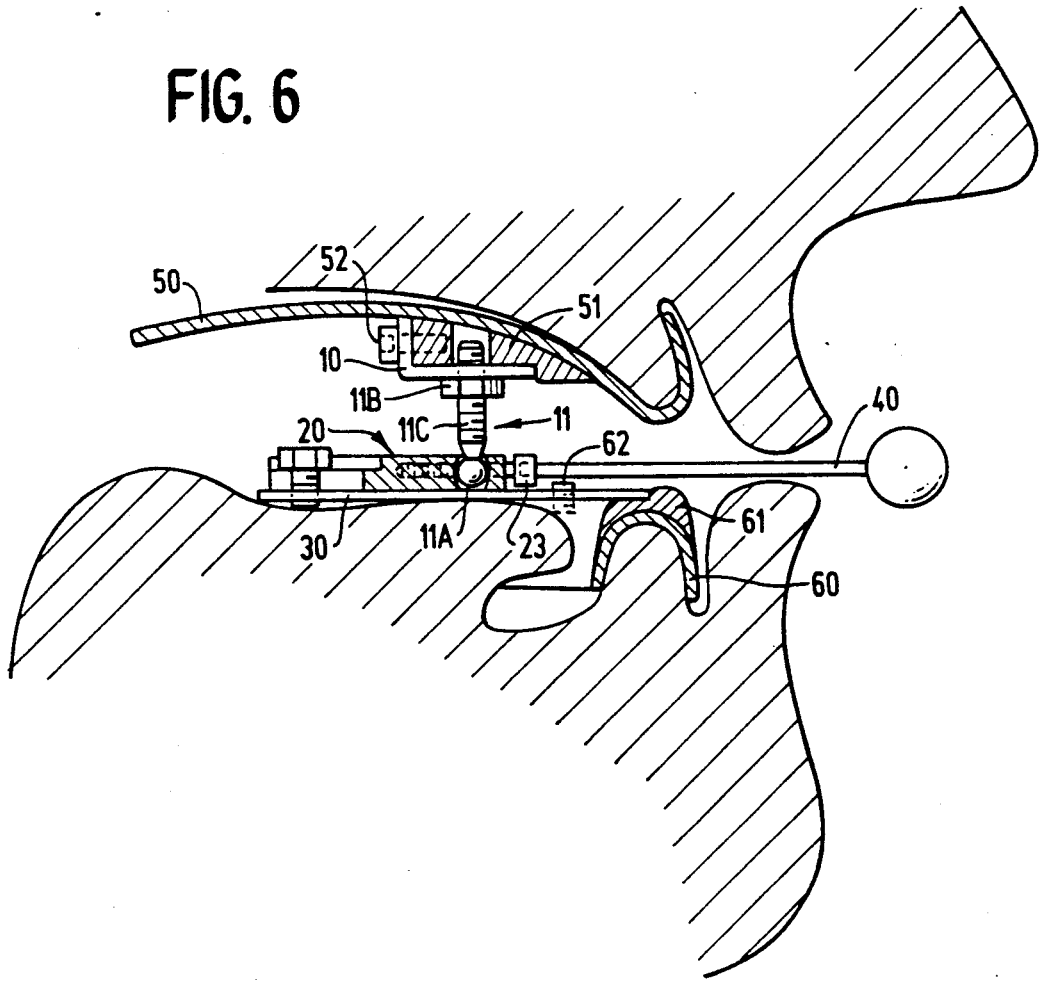

DEVICE FOR STATIC FIXATION OF THE JAW RELATION

BACKGROUND OF THE INVENTION

The present invention relates to a device for static fixation of the jaw relation, or relative position, in intraoral registration by means of a registration instrument set composed of a pin holder with a vertically adjustable stylus (support pin) for placement in a jaw, for instance the upper jaw, and a writing or recording plate with an alignment clamp (fixation plate) mounted thereon for placement in another jaw, for example the lower jaw. To make a dental prosthesis, the dentist must take jaw impressions, and these must be determined in their position both with respect to the jaw joint and in the relation to one another. To determine the relation between the joint and the jaw (axial relation), known techniques, employing headgear which are not the subject of this invention, are available.

Accordingly, the spatial relationship between the upper and lower jaws (jaw relation) must then be defined. To this end, it is for instance known, as disclosed in German Published, Non-Examined Patent Application DE-OS 28 25 470, to use a recording instrument set whose essential function is to produce a recording, based on certain specified patterns of motion between the upper and lower jaws of the patient, from which recording the proper jaw relation can be ascertained. A recording plate, i.e. a "jaw bite plate", is placed in the lower jaw and acts as a kind of blackboard for the support pin or stylus fixed in the upper jaw via a pin holder. This support pin arrangement is then capable of recording the jaw positions of interest for prescribed relative motions between the upper and lower jaws, and the result is typically an arrowlike structure, i.e. "symphysis track angle", on the basis of which the jaw relation can be determined.

To adjust the support pin on the recording plate, a displaceable clamp, or fixation plate, is provided, which has a recess for temporarily holding the tip of the support pin, that in turn is disposed in a predetermined relation with the afore-mentioned arrowhead-like marking.

Once the jaw relation has been ascertained from these measurements, this position is fixed, or keyed, for instance by introducing a hardenable material, i.e. impression plaster, between the recording plate and the pin holder by means of a syringe. This process is very uncomfortable for the patient, and very time-consuming for the dentist, as well as being expensive in terms of material. Moreover, for the duration of hardening of the impression material, it is no longer assured that the bite position will be maintained, nor can it continue to be monitored.

SUMMARY OF THE INVENTION

It is therefore an object of the present invention to attain a faster and simpler fixation of the jaw relation than has been heretofore possible.

According to the invention, the above and other objects are attained in that the stylus that is vertically locked on the pin holder can be locked in a stationary fashion in the ascertained jaw relation in the alignment clamp.

A recording instrument set in accordance with the invention is therefore intrinsically lockable and no longer needs keying by impression plaster or similar materials. After the proper jaw relation has been ascertained a single time and the alignment clamp has been accordingly fixed on the recording plate, locking between the alignment clamp and the support pin can be done with a few manipulations.

According to a further feature of the invention, the stylus is embodied as spherical in the form of a writing, or marking, ball on its lower end, and the alignment clamp has a pan bearing that is constructed such that when the pan bearing is opened, the writing ball can be introduced, and when the pan bearing is closed, it at least partly grips the writing ball from behind and firmly holds it.

The embodiment of the stylus as a writing ball is a particularly simple option for firmly holding the stylus in the pan bearing of the alignment clamp and also makes further simplifications in manipulation possible.

The spherical embodiment of the stylus permits the dentist to find the vertical dimension more simply without removing the recording instrument set, since the support pin on the ball can be grasped with the thumb and index finger and screwed to the intended height with the patient's mouth only slightly open. The patient is better able to compare the varying positions, which makes the ensuing recording phase easier and increases its precision.

Furthermore, the adjustment of the pan bearing for fixing the writing ball can easily be done from outside, by adjusting the entry cross section of the pan bearing, for instance with a suitable key; such a key can also easily be introduced toward the alignment clamps between the slightly opened jaws of the patient and makes locking possible.

Other features of the invention will be described below.

Exemplary embodiments of the recording instrument set according to the invention will now be described in detail with reference to the drawings.

BRIEF DESCRIPTION OF THE DRAWING

FIGS. 4 and 5 are plan views showing two further exemplary embodiments of alignment clamps according to the invention.

FIG. 6 is a side elevational cross-sectional view of the recording instrument set according to the invention in place in the oral cavity.

DESCRIPTION OF THE PREFERRED EMBODIMENTS

Figure 1:
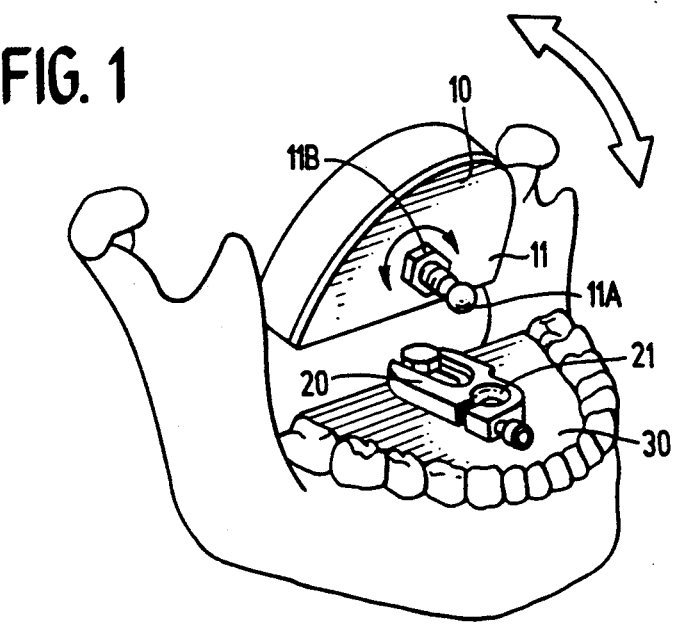
FIG. 1 is a schematic, perspective view of a recording instrument set according to the invention in place in the jaws of a patient.
Figure 2:
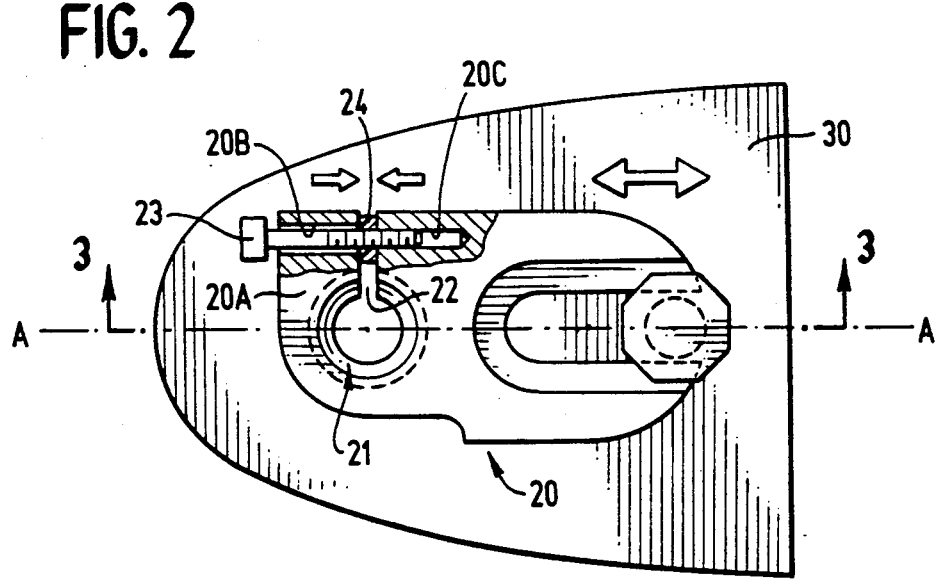
FIG. 2 is a plan view of the recording plate of the set of FIG. 1 with a first exemplary embodiment of an alignment clamp.
Figure 3:
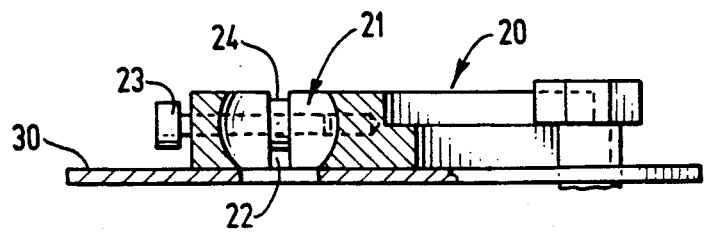
FIG. 3 is a longitudinal cross-sectional taken along the plane A—A of FIG. 2.

FIGS. 1-3 should not be understood as scale drawings particularly since the dimensions of the support pin and alignment clamp are shown disproportionately large so that their structure can be better understood.

In the first exemplary embodiment shown in FIGS. 1-3 and 6, a pin holder 10 is positioned relative to the upper jaw of the patient, as shown in FIG. 6, by an impression tray 50 which has been employed in the usual manner to take an impression of the teeth in the upper jaw, and by a mass of molding compound 51. i.e.

an autopolymerizate. Pin holder 10 is essentially an L-shaped metal plate with respect to which a threaded shaft 11C of a support pin or stylus 11 can be screwed in and out, so that the effective length of support pin 11 can be varied. Shaft 11C can be locked in a desired position with a lock nut 11B, which is necessary for adjusting the effective vertical dimension of support pin 11. Pin holder 10 is secured to the mass of molding compound 51 by two retention screws 52 which extend horizontally through the vertical leg of holder 10. This arrangement of screws 52 allows access for loosening pin holder 10 from the impression tray after removal from the mouth.

On the lower end of threaded shaft 11C, the stylus has a writing ball 11A, with which, in a manner known per se, certain relative motions between the upper and lower jaws are recorded on a recording plate 30, when disposed in the absence of an alignment clamp 20, in the lower jaw. Plate 30 may possibly be held in position relative to the lower jaw by a second impression tray 60 which is employed to obtain an impression of the teeth in the lower jaw by a mass of molding compound 61 which connects plate 30 to tray 60. Such relative motions for instance produce the arrow-shaped figure, or outline, mentioned in the introduction. In order for plate 30 to be securely positioned relative to tray 60, plate 30 may be fastened to tray 30 by two retention screws 62.

When plate 30 is in position relative to the lower jaw, the patient's tongue will be pressed downwardly and dorsally, as shown in FIG. 6 This aids proper positioning of the lower jaw for the registration procedure. The procedure according to the invention can be performed easily even on a patient with extreme macroglossia (enlarged tongue).

Depending on this outline, or target area, and the biting motions of the patient, which can be recognized for instance from coloration on the recording plate 30, the medically optimal jaw relation is then selected or determined, and the alignment clamp 20 is fixed relative to the recording plate 30 such that its pan bearing 21, disposed on its front end, comes to rest for instance above this target area.

The front part of alignment clamp 20, i.e. the part toward the front of the mouth, is embodied in the first exemplary embodiment (FIGS. 2 and 3) as a part which is curved, or bent, through an angle of approximately 90° and is elastically deformable. This front part terminates in a receiving block 20A that is separated from the other side of the alignment clamp 20 by a slit 22. Slit 22 extends from the outside of alignment clamp 20 as far as pan bearing 21, in such a way that a change in the width of slit 22 causes a change in the entry cross section of pan bearing 21. To attain this effect, a locking screw 23 is provided, which extends through the receiving block 20A parallel to the axis of symmetry A—A of recording plate 30 and engages a threaded bore 20C in the main part of alignment clamp 20 that is in alignment with a corresponding through bore 20B in the receiving block 20A. If the screw 23 is screwed in, the slit 22 consequently decreases in size, and the entry cross section of pan bearing 21 decreases accordingly. Slit 22 may be provided with a compressible elastic disc 24 which helps to open the pan bearing 21 when screw 23 is retracted.

The pan bearing 21 (FIG. 3) is shaped such that in its opening position, its entry cross section, or in other words the cross section at the surface of the alignment clamp 20, is slightly larger than the maximum cross section of the writing ball 11A, i.e. the cross section at its equator, so that when the two jaws close the writing ball 11A can plunge into the pan bearing 21 as far as its bottom without impairment. If the locking screw 23 is subsequently tightened, that is slit 22 becomes smaller, then the entry cross section of the pan bearing 21 becomes correspondingly smaller and its upper rim then at least partly encircles the back of the writing ball 11a and engages it from behind, so that the jaw relation is thus fixed. This locking can be done most simply, as shown in FIG. 6, by means of a key 40 which can be slipped onto or inserted into the head of locking screw 23 through the slightly opened mouth of the patient. The head of locking screw 23 may for instance have a hexagonal socket, in which case the operating end of key 40 correspondingly has the form of a socket wrench.

FIGS. 4 and 5 show two further exemplary embodiments of the alignment clamp 20 constructed to achieve reliable locking of the writing ball in the pan bearing 21.

In FIG. 4, there are provided two threaded pins, or set screws, 23A and 23B which pass through the wall of the pan bearing in its upper entry region and are disposed such that, when the writing ball is introduced into bearing 21, pins 23A and 23B can be advanced to reliably engage ball 11A from behind, i.e. from the upper jaw side, and thus "close" the pan bearing.

In FIG. 5, the alignment clamp 20 is made in two parts, with the separation line B—B passing through the center of pan bearing 21. The spacing between the two halves of the pan bearing is defined by means of two locking screws 23C and 23D disposed on both sides of the pan bearing, and operable to switch the pan bearing between "opened" and "closed" states.

Manipulation of the pins or screws 23A, B, C and D can likewise be done here via a key 40 having the form shown in FIG. 6. In principle, it is also conceivable to dispense with the more or less form-fitting receiving and fixation effected by a pan bearing as described above and to provide merely a frictional fixation, for example by means of a threaded pin acting on the stylus and guided in the alignment clamp.

In the drawings, the corresponding components are shown only schematically; the basic design of the recording instrument set is equivalent to the prior art, with the exception of the writing ball 11A and alignment clamp 20, and therefore need not be described in detail here.

FIG. 6 illustrates the instrument set at the moment of locking. After trays 50 and 60 are withdrawn from the mouth, the instrument set is disconnected from the trays by first removing screws 52 and then removing screws 62. The impressions can then be cast without any impediment. The instrument set can then be remounted to articulate the model.

This application relates to subject matter disclosed in German Application No. P 40 14 975.7, filed on May 5, 1990, the disclosure of which is incorporated herein by reference.

While the description above refers to particular embodiments of present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims rather than the foregoing description, and all changes which come within the meaning and range of equivalency of the claims are therefore intended to be embraced therein.

What is claimed is:

1. In a recording instrument set for static fixation of the relation between the upper and lower jaws of a patient in intraoral registration, the set comprising a pin holder with a vertically adjustable stylus for placement in a defined position relative to one jaw, a writing plate for placement in a defined position relative to the other jaw so that the stylus can contact the writing plate, and an alignment clamp mounted on the writing plate, the improvement comprising first locking means disposed for locking said stylus in a defined vertical position relative to said pin holder, and second locking means disposed for locking said stylus in said alignment clamp in a stationary position associated with an ascertained jaw relation, and wherein said alignment clamp is displaceable relative to said writing plate, is fixable in a selected position relative to said writing plate, and has an opening for receiving said stylus so that when said stylus is locked in said alignment clamp, said stylus contacts said writing plate at a point corresponding to the ascertained jaw relation.

2. An arrangement as defined in claim 1 wherein said stylus comprises a spherical ball disposed to contact said writing plate, and said alignment clamp comprises a pan bearing which delimits said opening and which is adjustable between an open condition for receiving said ball and a closed condition for firmly holding said ball in place in said bearing.

3. An arrangement as defined in claim 2 wherein said clamp is provided with a vertical slit associated with said pan bearing for permitting relative movement between parts of said clamp in order to adjust the cross section of said pan bearing, and said second locking means comprise a screw element disposed for permitting adjustment of the width of said slit.

4. An arrangement as defined in claim 3 wherein said clamp has a main portion and a curved portion, said curved portion is located toward the patient's mouth when said clamp is in place and is elastically deformable relative to said main portion of said clamp, and said curved portion includes a receiving block that delimits one side of said slit and has a through bore which receives said screw element.

5. An arrangement as defined in claim 4 wherein said writing plate has an axis of symmetry and said screw element extends approximately parallel to said axis of symmetry.

6. An arrangement as defined in claim 4 wherein said main portion of said clamp has a threaded bore which is in alignment with said through bore in said receiving block and said screw element engages said threaded bore after passing through said through bore.

7. An arrangement as defined in claim 6 further comprising an elastic disc filling said slit.

8. An arrangement as defined in claim 2 wherein said pan bearing has an entry cross section which in the open condition, is at least equivalent to the maximum cross section of said ball and, in the closed condition, is smaller than the maximum cross section of said ball.

9. An arrangement as defined in claim 2 wherein said second locking means comprises at least one threaded screw element extendible into the region of said pan bearing which receives said ball for engaging said ball in order to hold said ball in said pan bearing.

10. An arrangement as defined in claim 2 wherein said clamp is composed of two parts which delimit respective portions of said pan bearing and are movable toward and away from one another, and said second locking means comprises two locking screws engaging said two parts of said clamp and operable for varying the spacing between said two parts in order to adjust said pan bearing between its open and closed conditions.

* * * * *